United States Patent [19]

Nicholson

[11] Patent Number: 5,023,073

[45] Date of Patent: Jun. 11, 1991

[54] METHOD OF COMBATING FLUPROPADINE POISONING USING PHENOTHIAZINES

[75] Inventor: Russell A. Nicholson, Maple Ridge, Canada

[73] Assignee: Burroughs Wellcome Co., Research Triangle Park, N.C.

[21] Appl. No.: 420,260

[22] Filed: Oct. 12, 1989

[30] Foreign Application Priority Data

Oct. 13, 1988 [GB] United Kingdom ............... 8824050

[51] Int. Cl.$^5$ ............ G01N 33/15; A61K 31/54; A61K 31/445
[52] U.S. Cl. .................. 424/10; 514/224.8; 514/317; 514/823
[58] Field of Search ............ 424/10; 514/224.8, 317, 514/823; 540/547, 550; 546/192

[56] References Cited

FOREIGN PATENT DOCUMENTS 0041324 12/1981 European Pat. Off. .

OTHER PUBLICATIONS

J. Hyg. Comb., vol. 95, No. 2, 1985, pp. 502–512, A. P. Buckle "Field Trails of a New Sub-Acute Rodenticide Flupropadine . . . ".

Research Communications in Substances of Abuse, vol. 3, No. 3, pp. 287–295, (1982), M. R. Landauer et al., "The Effects of Chlorpromazine on the Lethality . . . ".

Chemical Abstracts, vol. 97, No. 19, Nov. 8, 1982, p. 261, Abstract No. 158014v, D. Kamencv et al., "Effect of Aminazin on the Agnostic Forms of . . . ".

Rowe, F. P. et al., Pen & Field Trials of Flupropadine Against The House Mouse, *J. Hyg.* 95(2):513–8, (1985).

Morgan, R. L. & Parnell, E. W., Flupropadine: A New Rodenticide Monogr.—*Br. Crop Prot. Counc.* 37 (Stored Prod. Pest Control):125–35, (1987).

*Primary Examiner*—Glennon H. Hollrah
*Assistant Examiner*—Gary E. Hollinden
*Attorney, Agent, or Firm*—Nixon & Vanderhye

[57] ABSTRACT

Antidotes to the rat poison flupropadine and substances acting in the same way include compounds which modulate (e.g. inhibit) aminergic systems in the gut or adrenal tissues. Such compounds include tricyclic antidepressants (e.g. chlorpromazine) and many others.

3 Claims, No Drawings

Marsh, R.E., Current (1987) and Future Rodenticides for Commgnsoal Rodent Control Bull. Soc. Vector Ecol. 13(1):102–107 (1988)

Merck Index 11th Edition 7793 pg. 1236

METHOD OF COMBATING FLUPROPADINE POISONING USING PHENOTHIAZINES

The present invention relates to antidotes to physiologically active compounds.

If a chemical compound is toxic to humans, pets or farm animals, it is always desirable for there to be an antidote. This is particularly so in the case of pesticides, which are distributed in the environment and are sometimes handled by persons who are unskilled in handling chemicals, and even more so in the case of pesticides used in bait formulations, since these are deliberately placed to be eaten by pests, and may accidentally be eaten by pets and children.

The compound flupropadine (1-(3,5-bistrifluoromethylphenyl)-3-(4-t-butylpiperidino)prop-1-yne), disclosed in EP-B-41234, is a potent killer of rats and other rodent vermin. Although the compound is less toxic than other rat poisons to other mammals, there is still a need for an antidote. The present invention provides antidotes to flupropadine and related compounds.

One aspect of the present invention provides a method of combating poisoning in mammals by flupropadine or related compounds, the method comprising administering an effective dose of a compound which modulates aminergic systems in gut or adrenal tissues.

5-HT (5-hydroxytryptamine, serotonin) and noradrenaline (NA) have a number of important physiological roles, including those of neurotransmitter and neuromodulation in the brain and elsewhere, particularly in the gastrointestinal tract (for example the upper G.I. tract) and adrenal gland.

It is thought that 5-HT and noradrenergic systems are the most important and that it is the inhibition of flupropadine-induced depletion of these amines in the gastrointestinal tract and adrenal tissue which confers the desired antidote properties. Inhibition of release of these amines may also be effective.

Suitable compounds include; tricyclic anti-depressants, including the phenothiazines and thioxanthines, such as imipramine, desipramine, nortriptyline, proptripyline, doxepin, chlorpromaxine, triflupromazine, prochlorperazine, promazine, promethazine, thiethylperazine, thioridazine, perphenazine, fluphenazine, acetophenazine, trifluoperazine, chlorprothixene, and thiothixene and others, such as citalopram and fluoxetine. Suitable compounds further include:

Desmethylcitalopram (Lu 11-109), Didesmethylicitalopram (Lu 11-161), Citalopram-N-oxide (Lu 11-305), CGP 6085 A, Alaproclate, Paroxetine (FG 7051), Zimelidine (H 102/09), Ro 11-2465, Femoxetine (FG 4963), Norzimelidine, Trazodone, chlorimipramine, YM-08054-1, Cocaine, Trimipramine, Butriptyline, Iprindole, Opipramol N-methyl protriptyline, Fluotracen, Lilly 5182, Melitracen, Mazindol, Mianserin, Viloxazine, Dibenzepine, Desmethylchlorimipramine, Nomifensine, Maprotiline, Talopram (Lu 3-010), Litracen, Talsupram (Lu 5-003), and Hydroxymaprotiline (C49-802 B-Ba). Pharmaceutically acceptable salts of all these compounds are included within the scope of the invention.

Chlorpromazine, imipramine, citalopram and nortriptyline are the preferred compounds of the invention, particularly the first three, and especially chlorpromazine.

Any of the antidotes of the invention may be combined with other pharmacologically active compounds, if appropriate, in order to obtain additive or synergistic effects.

The dose of the antidote(s), the dosage regime and total period of treatment will depend upon the amount of flupropadine which has been ingested, the animal in question and the antidote being used. In general, a relatively long period (at least a week) of treatment is preferred, partly because flupropadine has a prolonged effect and partly because, as is known, some of the antidotes take days or more to exert their physiological effects.

A particular advantage of at least most of the antidote compounds listed above is that they have been used for human treatment in other contexts for many years and have been prescribed widely. Thus, their effects and toxicities are known, and their use in accordance with the present invention is thereby facilitated. By the term "combating poisoning" we include the administration of the antidote in cases of suspected but unconfirmed poisoning.

The antidote compounds may be administered in any suitable way consistent with their properties, for example orally, rectally, sub-cutaneously, intra-muscularly, nasally or transdermally. For prolonged action, a sub-cutaneous implant, whether a simple depot or a mini-pump, may be suitable. The compounds may be administered in such forms and at such dosage rates as may be thought by a physician to be effective and safe. However, reference may also be made to current editions of such standard works as "The Pharmacological Basis of Therapeutics", Ed Goodman & Gilman, the British National Formulary, the British Pharmacopoeia, the U.S. National Formulary and the US Pharmacopoeia.

The antidote compounds may be used in connection with poisoning by flupropadine, in any form, by flupropadine analogues, or by any other poison having the same mode of action as flupropadine. The term "or related compound" is used herein to mean all such compounds.

As the antidote compounds listed above are known compounds, reference may be made to published sources for their syntheses. A further aspect of the invention provides the use of a compound which modulates aminergic systems in the gut or adrenal gland in the manufacture of a medicament to combat poisoning by flupropadine or related compounds.

Flupropadine and related compounds may be sold together with an antidote of the invention, optionally with a hypodermic syringe or other means of administering the antidote. Hence, a further aspect of the invention provides a kit comprising (a) flupropadine or a related compound and (b) a compound which modulates an aminergic system in gut tissue or adrenal tissue.

EXAMPLES

EXAMPLE 1

Protective effect of Imipramine, Citalopram and Chlorpromazine against poisoning induced by the rodenticide Flupropadine in the rat Female rats administered in a single oral dose of the rodenticide flupropadine (100 mg/kg) die usually within 6 to 9 days as a result of severe disturbances to the gastrointestinal tract. Similar effects have been observed in mice. Imipramine (12.5 mg/kg), citalopram (30 mg/kg) and Chlorpromazine (8.1 mg/kg) when administered orally (twice daily) to rates for 17 days following treatment with the rodenticide prevented the onset of G.I. symptoms and death. Protection is also observed when imipramine, citalopram and chlorpromazine are applied sub-cutaneously by continuous infusion mini-pumps prior to dosing with flupropadine.

EXAMPLE 2

Formulations

Chlorpromazine

For human use, chlorpromazine can be made up in known ways as the hydrochloride in tablets containing 10-200 mg active ingredient, sustained release capsules of 30-300 mg, syrups of 10 mg/5 ml or concentrates of 30-100 mg in 10 ml. A single intramuscular dose is typically 25-50 mg which may be given 4 to 10 times a day. However, the dose may be between 5 and 5000 mg, typically 25-2000 mg and usually 200-800 mg.

Other compounds may be presented in their usual dosage forms, such as prochlorperazine as the edisylate or maleate and fluphenazine as the hydrochloride, enanthate or decanoate.

What is claimed is:

1. A method of using phenothiazines to combat poisoning in mammals by flupropadine, the method comprising administering to said mammal an effective dose of a phenothiazine.

2. The method of claim 1 in which the phenothiazine is chlorpromazine, triflupromazine, prochlorperazine, promazine, promethazine, thiethylperazine, thioridazine, perphenazine, fluphenazine, acetophenazine or trifluoperazine or a salt thereof.

3. The method of claim 2 in which the phenothiazine is chlorpromazine or a salt thereof.

* * * * *